United States Patent [19]

Savini

[11] 4,032,578
[45] June 28, 1977

[54] PROCESS FOR THE MANUFACTURE OF ALDEHYDES AND HDA AND OTHER ALCOHOLS BY ALDOL CONDENSATION

[75] Inventor: Charles G. Savini, Warren, N.J.

[73] Assignee: Exxon Research and Engineering Company, Linden, N.J.

[22] Filed: Jan. 7, 1976

[21] Appl. No.: 647,150

Related U.S. Application Data

[63] Continuation-in-part of Ser. No. 547,475, Feb. 6, 1975, abandoned, which is a continuation of Ser. No. 317,615, Dec. 22, 1972, abandoned.

[52] U.S. Cl. .......................... 260/601 R; 260/638 B
[51] Int. Cl.² ................. C07C 47/02; C07C 45/00; C07C 29/14
[58] Field of Search .................... 260/601 R, 638 B

[56] References Cited

UNITED STATES PATENTS

| | | | |
|---|---|---|---|
| 2,485,989 | 10/1949 | Smith | 260/601 R |
| 2,757,200 | 7/1956 | Jones et al. | 260/638 HF |
| 2,809,220 | 10/1959 | Mertzweiller et al. | 260/638 HF |
| 2,810,762 | 10/1957 | Ernst et al. | 260/635 A |
| 2,848,498 | 8/1958 | Mention | 260/638 B |
| 3,148,218 | 9/1964 | Heimsch et al. | 260/601 R |
| 3,432,557 | 3/1969 | Wile | 260/601 R |

FOREIGN PATENTS OR APPLICATIONS

2,058,532   5/1971   France .......................... 260/638 B

Primary Examiner—Joseph E. Evans
Attorney, Agent, or Firm—C. Leon Kim

[57] ABSTRACT

A new process for the manufacture of aldehydes by aldol condensation using a feed consisting of crude, high conversion, demetalled conventional oxo product is described. In another embodiment a new process for the manufacture of hexadecyl alcohol and related alcohols using the above-described feed is also set forth. The process is a uniphase aldol condensation process utilizing small quantities of basic catalyst and operating above certain minimum threshold temperatures. The process is operable with crude oxo feeds that contain as much as 40% by weight acetals. Process conditions are described which enable reversion of the acetals to aldehydes and alcohols thereby allowing concurrent condensation of reactive components with high selectivities to the product alcohols and aldehydes. The products of the process, such as hexadecyl alcohol, are well known and have many uses, such as in the formulation of cosmetic products.

8 Claims, 1 Drawing Figure

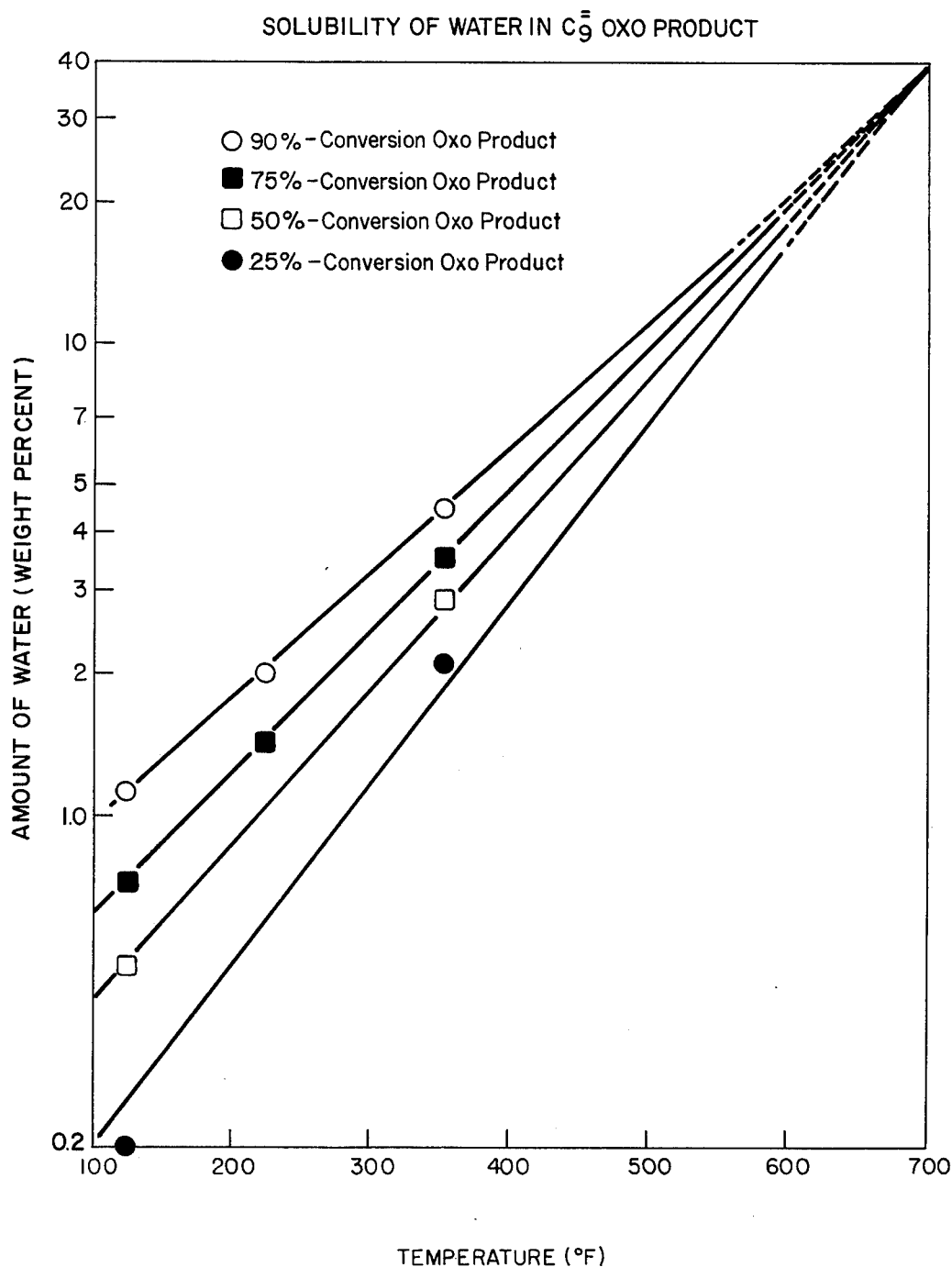

PROCESS FOR THE MANUFACTURE OF ALDEHYDES AND HDA AND OTHER ALCOHOLS BY ALDOL CONDENSATION

CROSS-REFERENCE TO RELATED APPLICATIONS

This application is a continuation-in-part of pending U.S. Ser. No. 574,475, filed Feb. 6, 1975, now abandoned, which is in turn a continuation of U.S. Ser. No. 317,615, filed Dec. 22, 1972, now abandoned.

FIELD OF THE INVENTION

This invention relates to a novel process for the manufacture of hexadecyl alcohol via aldol condensation using crude, high conversion, demetalled, conventional oxo product as feed followed by hydrogenation and purification. More particularly, the invention relates to an improved aldol condensation process which represents a viable alternative to presently employed aldox processes.

BACKGROUND OF THE INVENTION

The manufacture of hexadecyl alcohol and related alcohols is presently commercially produced via the aldox process whereby overall produce yields are approximately 20%. Additionally, the commercially employed process produces severe operating problems and significantly reduces the production of the conventional oxo alcohol. Alternate conventional systems employ low temperature two-phase and additionally may be characterized as high basicity systems. Selectivities for the conventional systems have never appreciably exceeded about 60% due to the side reactions which occur at process conditions required to achieve acceptable reaction rates.

DESCRIPTION OF THE PRIOR ART

Aldolization processes are well known in the art and provide a ready means for preparing aldehydes and alcohols from compounds containing olefinic unsaturation. These processes generally involve condensation of two moles of aldehyde to produce a hydroxy aldehyde. The lower aldols are readily dehydrated to the corresponding unsaturated aldehyde which upon reduction forms the saturated alcohol. One of such processes is described adequately in U.S. Pat. No. 3,454,649 where high molecular weight alcohols containing 2 or more carbon atoms than twice the number in the olefin feed are produced. The feed employed is the oxo reaction product which is mixed with an oil soluble Group II metal compound such as magnesium oleate. The combined feed is then passed to a heating zone where dimeric aldehydes are produced. After demetalization, the reaction product is hydrogenated under conventional hydrogenating conditions in the presence of hydrogenation catalysts to provide dimeric alcohols. In U.S. Pat. No. 2,810,762, a process for the preparation of glycols and dimeric alcohols from aldehydes is described wherein the aldehyde feedstocks employed are feedstocks contaminated with minor amounts of alcohols and other impurities. The decobalted and dried crude aldehyde products from an oxo process are passed to a reaction vessel and mixed with a slurry of sodamide in a temperature range of about 100°–250° F where aldolization occurs. The crude condensation product is then converted to mono- and dihydric alcohols under conventional hydrogenation conditions.

Also, U.S. Pat. No. 2,820,067 describes a process for the preparation of high molecular weight alcohols from low molecular weight olefins by a novel modification of the aldehyde synthesis reaction. This modification resides in the treatment at elevated temperatures and low pressures of the aldehyde products from the carbonylation process in the presence of zinc salts for extended periods which is then followed by hydrogenation to produce high yields of dimeric primary alcohols. U.S. Pat. No. 3,248,428 discloses a process for producing alpha, beta unsaturated carbonyl compounds of increased molecular weight by the condensation of carbonyl compounds of relatively low molecular weight at elevated temperatures with a catalyst comprising an insoluble reaction product of molybdenum oxide and magnesium oxide. Finally, U.S. Pat. No. 2,848,498 describes a process for the production of aldols, ketols and unsaturated oxo compounds from one or more saturated oxo compounds as feeds. The process comprises mixing a stream of a saturated oxo compound or compounds with a stream of an aqueous alkaline condensation agent. For the most part, the abovedescribed processes result in selectivities considerably less than 100% and during operation require significant controls to avoid undesirable side reactions and may require catalyst recycle and the use of special materials which resist corrosion of the high caustic concentrations. There is, therefore, a need for an efficient, highly selective route to aldehydes and their corresponding hydrogenated aldol saturated alcohols which avoids many of the processing problems of conventional systems.

SUMMARY OF THE INVENTION

In accordance with the present invention, a twostep process for the manufacture of aliphatic alcohols is described. The process comprises contacting an aldehyde or acetal-containing feedstream with a lower level of basic catalyst selected from the group consisting of Groups I-A and II-A hydroxides, soaps, alkoxides, phenoxides; quaternary ammonium hydroxides, choline and the like. The contacting is carried out in the presence of a controlled amount of water and a temperature in excess of 200° F. to thereby provide a uniphase reaction media whereby aldolization of the aldehyde feedstream takes place. The amount of water present in the aldolization media must be controlled such that it does not exceed the water solubility of said media so as to maintain a homogeneous liquid-phase aldolization mixture. The product from this step is then hydrogenated over Raney-nickel catalyst at temperatures of 300° to 400° F. and hydrogen partial pressures of 1–40 atm. to produce a yield of saturated alcohols.

By the term "aldolization" as used above is meant the condensation reaction in which two molecules of aldehyde react and bond one to the other in a way such that the alpha carbon of the first aldehyde molecule becomes attached to the carbonyl carbon of the second. The following illustrative equation demonstrates this aldol condensation and subsequent dehydration.

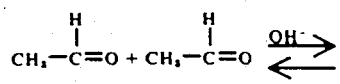

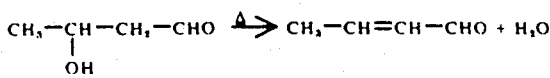

The extent of aldol dehydration is dependent upon the specific process conditions of the reaction system. As described above, the feed may broadly be referred to as any aldehyde-containing feedstream. More particularly, feedstreams such as pure aldehyde or dilute feedstreams containing aldehydes with or without associated impurities may be used in the present invention. Preferably, the feedstream employed is a crude, demetalled, high conversion oxo product stream from a typical oxo reactor. Such a crude oxo feedstream typically contains 20% hydrocarbons, 40% aldehydes, 20% alcohols, and 20% acetals.

The novelty and improvement of the present invention over conventional aldol methods resides in the substitution of high temperatures for the conventional high basicity concentration requirement. By using higher temperatures, such as will be described hereinafter in the presence of a controlled amount of water, lower levels of basic catalysts may be employed; and higher aldehyde conversions to the aldol product will be generated because of the reversion of the acetal species present in the feed and the avoidance of undesirable side reactions. It has unexpectedly been discovered that acetal reversion to the aldehyde precursor can be effectively carried out under slightly basic conditions in the presence of a controlled amount of water. An additional advantage gained by the operation of the present inventive process is that impure aldehyde feeds may be employed without substantially affecting overall selectivities.

Another embodiment of the present invention is the employment of a uniphase reaction system. This uniphase system, which is obtained by monitoring processing conditions, such as water levels, temperature, and the like, has distinct advantages in the operation of an aldol condensation process. Some of the advantages of the uniphase oxo aldol processing at preferred process conditions, (hereinafter described as UFOA) not otherwise obtainable with conventional technology are as follows: (1) The elimination of emulsions in the aldol reactor and in subsequent processing steps; (2) substantial lower energy costs because of minimal mixing requirements since the reaction takes place in a single phase; (3) higher selectivity to the desired product as well as the use of relatively inexpensive materials of construction for equipment fabrication due to the low caustic levels required; (4) plug flow reactors, e.g., tubular or packed-fed reactors, may be used if desired; (5) catalyst recovery, recycle and associated handling are eliminated since small quantities of catalyst are used in a single pass system; (6) pure aldehyde feeds can be processed with high selectivity; and (7) finally there is markedly lower investment and operating costs per given plant capacity.

As described above, the contact of the aldehyde-containing feedstream with the basic catalyst may take place in the presence of a controlled amount of water where the aldehyde-containing feedstream also contains a certain amount of acetal. The amount of water present in the aldolization mixture should be within the solubility limit of said mixture so as to maintain a uniphase reaction media. The following equilibrium shows that the presence of water helps bring about the acetal reversion to the aldehyde precursor and consequently higher yields of aldol product:

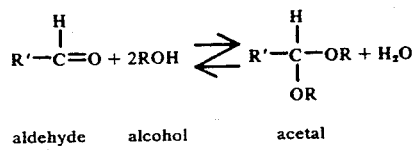

aldehyde   alcohol   acetal

The basic catalyst employed is one generally to be described as a weak to moderate base or a dilute solution of a strong base. Typically, Groups I-A and II-A hydroxides are employed. Equally operable are Groups I-A and II-A soaps, such as sodium stearate. Moreover, Group I-A and II-A alkoxides and phenoxides are applicable. Alkoxides may be described as having the formula RO-Na$^+$ where R is an alkyl group while phenoxides may be described as having the formula PhO-Na$^+$ where Ph is a phenyl group. Nonlimiting representative examples of suitable catalysts include Groups I-A and II-A oleates, stearates, octoates, and tallates; Group I-A and II-A acetates; sodium hydroxide, potassium hydroxide, quaternary ammonium hydroxides and the like.

Catalyst demands are extremely small and consequently, the need for catalyst recycle operations is avoided. Low catalyst concentration has other beneficial effects, included among these are high product selectivity. In fact, materials such as sodium acetate or sodium stearate, can be used in the aldol condensation to give product with the equivalent selectivity and reactivity as a caustic sodium hydroxide base system. While any of the above-referred to materials may be used as a catalyst, preferred as a catalyst is the use of dilute caustic.

As described above, where acetals are present in the feedstream, the addition of water in a limited amount is critical to bring about the reversion of the acetal species to the aldehyde.

In a preferred embodiment of the instant invention, an aqueous solution of a basic catalyst, which solution contains water in an amount within the solubility limit of the aldolization mixture, is used to obtain a uniphase aldolization media. The water solubility in the aldolization mixture depends on various factors such as the specific feed employed and the reaction temperature. As shown in the attached diagram, the water solubility in a crude $C_9^-$ oxoproduct, which may be used as the aldol feedstock, increases with the temperature. In general, the water solubility in a crude, demetalled $Cn^-$ oxo product ($n=5,6, \ldots, 12$) increases by aproximately one weight percent per unit decrease in the olefinic feed carbon number, as summarized in Table Ia given below.

TABLE Ia

WATER SOLUBILITY IN CRUDE OXO PRODUCT[1] AT 500° F.

| Oxo Product | Solubility[2] | Oxo Product | Solubility |
|---|---|---|---|
| $C_6HO$ = | 13.5 | $C_{10}HO$ = | 9.5 |
| $C_7HO$ = | 12.5 | $C_{11}HO$ = | 8.5 |
| $C_8HO$ = | 11.5 | $C_{12}HO$ = | 7.5 |
| $C_9HO$ = | 10.5 | $C_{13}HO$ = | 6.5 |

Notes:
[1] Data pertain to "high conversion" oxo product; i.e., 75-90 percent olefin conversion in oxo
[2] Solubility expressed as wt. percent $H_2O$; specific gravity of oxo product = 0.8 vs. 1.0 for water at ambient temperatures.

The invention is operable over a wide range of process conditions as described herein. However, the most critical process variable is process temperature. In order to achieve reactivity and maximum selectivities, sufficient for a good commercial operation in the absence of the conventional high base concentration requirements, a minimum threshold temperature of approximately 200° F. is necessary. In general, however, the process is operable from 150°–1,000° F., preferably from 300°–800° F., most preferably 500°–700° F.

The amount of base to be employed, as described above, is the minimal amount necessary to bring about the desired reactivity and selectivity. However, in general, the amount of base present during the course of a reaction will be from 0.01 to 3.0 wt. %, preferably from 0.05 to 2.0 wt. %, and most preferably from 0.1 to 1.0 wt. % based on amount of feed.

Residence times, in general, depend upon process conditions such as temperature, water level, etc. However, satisfactory yields are obtainable with residence times of between about 0.08 to 5 hours, preferably from about 0.25 to 1.5 hours. The process is carried out at the autogeneous pressure of the reaction system and is temperature dependent. Additionally, however, the process may be carried out at pressures which are subatmospheric or superatmospheric.

The hydrogenation of the aldol product to produce the saturated alcohol is carried out under conventional conditions and using conventional catalysts. For example, hexadecyl alcohol precursor is effectively hydrogenated at 2800 psig with a Harshaw 3250T supported nickel catalyst. Hydrogenations may be carried out using any of the conventional hydrogenation catalysts including materials such as Raney-type nickel at pressures of from 400–600 psig. The products of the two-step process are saturated alcohols having twice the number of carbon atoms as the original aldehyde feed. For example, octylaldehyde is the feed employed when hexadecyl alcohol is the alcohol desired.

It should be noted that the overall solubility of water in an aldolization mixture does not, in general, change significantly with the extent of aldolization, if the aldolization is conducted at a higher temperature, i.e., above about 300° F., and a crude oxo product, which contains a substantial quantum of acetals, is employed. This is partly because a possible decrease in the water solubility due to the formation of aldols is largely counterbalanced by an increase in the water solubility attributable to the alcohols generated by the acetal reversion. Furthermore, as indicated in the accompanying Figure, the water solubility of an aldolization mixture tends to converge to a limit point, regardless of its composition, as the mixture temperature increases.

In addition, the level of water present in the aldolization mixture remains substantially constant throughout the aldolization process, for the portion of water consumed in reverting the acetals back to aldehydes and alcohols is substantially replenished by the water generated by the alcohol dehydration. However, should one desire to continuously monitor the water solubility and the water content of the aldolization mixture at a given conversion and a chosen temperature, a standard Karl Fischer titration method as described in Example 7 may be employed.

Widely practiced means of introducing water may be employed in order to readily obtain a uniphase aldolization media. For example, a sparger or a quench distributor, which may be provided in the aldolization reactor, can be utilized in introducing an aqueous solution of a basic catalyst, which solution contains a controlled amount of water, into the feedstream. If the feedstock is preheated in a separate container before it is fed into the aldolization reactor, the aqueous catalyst solution can be homogeneously mixed with the feedstock in this preheater with the use of a static mixer or other contacting devices known in the art.

The overall process may be more readily understood by reference to a typical process for manufacture of hexadecyl alcohol. Feed for the process is the crude, demetalled $C_8$ aldehyde stream produced in a conventional oxo alcohol plant using UOP heptenes as the olefin feed source. Feedstream composition for HDA manufacture via UFOA processing is as follows: lights (10 wt. %), $C_8HO$ (49 wt. %), $C_8OH$ (24 wt. %), $C_{16}$ (1 wt. %), $C_{24}$ acetal (16 wt. %), and trace heavy components.

Aldolization is carried out in the following manner. Three volume percent of 2.5 normal sodium hydroxide, which contains water below the solubility limit of the feed at the chosen temperature, i.e. 600° F., is continuously added to a crude, $C_8HO$ feedstream. This composite stream is pumped through a reactor preheater to attain a temperature of 600° F. A static mixer is employed to promptly bring the mixture to a homogeneous state. Effluent from the preheater enters an insulated, packed-bed reactor operated in the down-flow configuration. Space velocity through the condensation reactor is 2 v/hr/v. Composition of the reactor product stream is: lights (10 wt. %), $C_8HO$ (24 wt. %), $C_8OH$ (34 wt. %), $C_{16}$ (30 wt. %), $C_{24}$ acetal (2 wt. %), and trace heavy components.

Quenching and washing of the aldol product stream is carried out by a single unit operation. Water at ambient temperature is continuously injected into the aldol reactor effluent stream at a concentration of 10 volume percent based on the reactor flow volume. A static mixer in the transfer line from the condensation reactor to a settling drum provides adequate contacting of the product and water streams. Phase separation occurs in the disengaging drum which operates with a residence time of 5 minutes. Process temperature in the settling drum is 350° F.

Aqueous phase from the settling drum is sent to the oxo plant environmental conservation stream treatment facilities in order to remove all pollutants. The organic phase from the drum is compressed and transferred to hydrogenation facilities.

Hydrogenation is carried out in fixed bed reactors operating at 2800 psig over NiWS catalyst at 350° F. and with a space velocity of 1.0 v./hr./v. Composition of hydro product is as follows: lights (11 wt. %), $C_8HO$ (trace), $C_8OH$ (59 wt. %), $C_{16}OH$ (30 wt. %), and trace heavy components.

Separation and purification of hydro product is carried out in a standard distillation train operating under vacuum.

Overall yields obtained with the UFOA process scheme are 57 lbs. isooctyl alcohol and 28 lbs. hexadecylalcohol per 100 lbs. of crude oxo feed of the composition stated above.

To further illustrate the process of the present invention, the following examples are provided; however, it is to be understood that the details thereof are not to be regarded as limitations as they may be varied as will be understood by one skilled in the art.

EXAMPLE 1

Crude, demetalled, oxo product produced from UOP heptene polymer was the feedstream for all reactions summarized in Table I. Feed and product compositions for the experiments described herein were determined by G.C. using n-nonane as an internal standard for instrument calibration. Pertinent analyses are presented below.

Water, catalyst, and feed were mixed in the amounts shown and the composite mixture was charged to a 1 liter autoclave at ambient pressure and temperature. After the reactor was flushed with inert gas, it was sealed and rapidly heated to 500° F., forming a uniphase mixture. Temperature was controlled (±5° F.) at this level by standard control instrumentation. Sampling of the reaction product was carried out at the process temperature and residence time shown in Table I and the compositions of the product streams were determined according to the G.C. procedure previously described.

Results show: (1) aldehyde components in a crude, demetalled, $C_8$ oxo feedstream can be condensed at high temperature with small quantities of base catalyst in a single phase reaction environment with high selectivity; (2) aldolization to the desired dimers is effectively catalyzed by small amounts of base; thermal treatment of crude oxo product does not produce significant yields of $C_{16}$ dimers (Run I vs. Run III); (3) acetal components in the crude feedstream revert to alcohol and aldehyde at the above process conditions and concurrent production of commercially valued products is achieved; and (4) the reaction can be carried out with different classes of base catalyst (e.g., 0.02 wt. % NaOH on feed and 1.07 wt. % benzyl trimethyl ammonium hydroxide on feed).

amount of water is within the solubility limit of the reaction mixture.

Run II was carried out in a 2000 ml round bottomed glass flask continuously purged with a very small amount of inert gas ($N_2$) to eliminate oxygen from the system. A reflux condenser was fitted to the top of the reaction flask and chilled water was circulated through the shell side and its internal cooling coils in order to eliminate loss of organic components from the system. The reaction system was vented through the reflux condenser, and the $N_2$ purge leaving the reflux condenser was discharged at essentially atmospheric pressure.

Procedures used for Run II were as follows: Approximately 500 cc of aqueous caustic solution was prepared by slowly dissolving reagent grade NaOH (164 gms) in water (418 gms). This caustic solution was added to the glass reaction vessel through a feed port located on the top of the 3-necked, round bottom flask. Crude oxo feed (500 cc) of composition shown in Table II was also added to the reaction vessel through the feed port. The reaction vessel was sealed, purged with inert gas, and heated by an electrical heating mantel surrounding the flask. Vigorous stirring was provided by a standard flask mixer powered by an external air motor. The reaction was conducted at 195° F. for 4 hours. It should be noted that the amount of water present in the reaction mixture exceeded the solubility limit of the reaction mixture; hence, a two-phase reaction media was formed. Product was sampled at process temperature and analyzed by the G.C. procedure previously defined.

Run III was carried out with crude, demetalled oxo product of composition shown in Table II. A single-phase reaction environment was employed through the use of an alcohol diluent.

TABLE I

HDA PRODUCTION FROM CRUDE, HIGH CONVERSION, DEMETALLED, $C_8$ OXO PRODUCT VIA UFOA PROCESSING

| Aldol Step | Run I | Run II | Run III |
|---|---|---|---|
| ● Reaction Conditons: | | | |
| + Reactor Type | Batch | Batch | Batch |
| + Isothermal Reaction Temperature (° F) | 500 | 500 | 500 |
| + Res. Time (hrs) | 5 | 4 | 4 |
| ● Feed: | | | |
| + $C_8$HO Hydro Feed (cc) | 500 | 500 | 500 |
| + $H_2O$ (gms) | 25 | 15 | 25 |
| + Catalyst (type) | NaOH | $(\phi CH_2)N(CH_3)_3OH$ | None |
| + Catalyst (gms) | 0.1 | 4.3 | — |

Aldol Feed and Product Compositions

⟵———Pct. by Weight———⟶

| Component | Aldol Feed | Run I Prod. | Run II Prod. | Run III Prod. |
|---|---|---|---|---|
| lights | 10.5 | 9.6 | 10.3 | 10.8 |
| $C_8$ HO | 49.0 | 22.2 | 34.7 | 44.3 |
| $C_8$OH | 24.0 | 33.9 | 33.1 | 29.8 |
| $C_{16}$ Prod. | 2.6 | 32.4 | 17.5 | 6.5 |
| $C_{24}$ | 14.0 | 2.1 | 2.7 | 4.8 |

$\phi$ = phenyl.

EXAMPLE 2

Crude, demetalled, oxo product produced from UOP polymer was the feed for all reactions (Runs I, II and III) shown in Table II. Feed and product analyses for these experiments were determined by the standard G.C. procedure set forth in Example 1.

Run 1 was carried out in a 1 liter autoclave according to the procedures set forth in Example I wherein the Procedures employed for Run III follow. Base catalyst was mixed with the alcohol and the oxo product component of the feed was added and thoroughly mixed. The composite reaction feed was placed in a standard 3 liter steel rocker bomb and purged with inert gas ($N_2$). The closure of the reaction vessel was sealed and the vessel placed within a standard rocker cradle. Rapid heating was provided by an electrical heating mantel surrounding the reaction vessel. Temperature was maintained (±5° F.) by conventional control instrumentation at the desired process temperature for the time interval shown below. After the desired residence time was reached, the reaction vessel was rapidly cooled by chilled water flowing through an internal cooling coil. The product was removed from the reactor and analyzed by G.C.

Results show: (1) yields of valued product ($C_8$ alcohol and dimer alcohol precursor) are substantially greater using the claimed UFOA process technique; conventional 2-phase aldolization (Run II) using the high basicity required to attain reasonable reactivity and the uniphase reaction system (Run III) using an alcohol solubilizing diluent give substantially lower product yields; (2) stable emulsions characteristic of conventional two-phase aldolization reaction systems using $C_7^+$ aldehyde feeds (e.g., Run II) are not formed in the UFOA process claimed herein (e.g., Run I); 3) acetals contained in crude oxo feed do not revert to alcohol and aldehyde precursors in conventional aldol reaction systems (e.g., Runs II and III) and furthermore, the classical aldolization reaction systems using high basicity catalysts generate measurable quantities of heavy boiling components.

EXAMPLE 3

Feed materials for the experiments summarized in Table III were crude, demetalled, oxo products produced from various molecular weight fractions of a commercial UOP polymer stream. Compositions of feed and product streams were obtained by G.C. in the manner as set forth in Example 1. Analyses are presented below.

Each experiment was carried out using 1500 cc of oxo feed. The procedure of Example 2, Run III was utilized for each run except that water was employed in place of isopropyl alcohol, and the reactions were performed in the same process equipment. Oxo product feed was mixed with aqueous caustic in the amounts shown below and the composite feed was placed within a 3000 cc steel rocker bomb. These reactions where then performed in the rocker bomb according to the procedures set forth in Example 2, Run III.

The results of this Example are set forth in summary fashion in Table III and show that the UFOA condensation carried out by the present invention is applicable to a wide molecular weight range of crude oxo product streams used as feedstreams.

TABLE II

NEW ALDOL PROCESS VS. CONVENTIONAL ALDOL CONDENSATON

|  | UFOA Run I | Run II | Run III |
|---|---|---|---|
| ● Reaction Conditions: (Batch Reactions) | | | |
| + Isothermal Reaction Temperature (° F) | 500 | 195 | 180 |
| + Res. Time (hrs.) | 5 | 4 | 4 |
| ● Feed: | | | |
| + $C_8$HO Hydro Feed (cc) | 500 | 500 | 500 |
| + $H_2O$ (gms) | 25 | 418 | 82 |
| + NaOH Catalyst (gms) | 0.1 | 164 | — |
| + KOH Catalyst (gms) | — | — | 82 |
| + Isopropyl Alcohol (gms) | — | — | 410 |

● Feed and Product Compositions (% by wt.)

| Component | UFOA Run I Feed | UFOA Run I Product | Run II Feed | Run II Product[1] | Run III Feed | Run III Product[4] |
|---|---|---|---|---|---|---|
| lights | 10.5 | 9.6 | 22.6 | 23.9 | 23.1 | 25.7 |
| $C_8$HO | 49.0 | 22.2 | 45.7 | 14.5 | 49.1 | 4.5 |
| $C_8$OH | 24.0 | 33.9 | 17.0 | 15.8 | 17.8 | 10.7 |
| $C_{16}$ Prod. | 2.6 | 32.4 | 3.4 | 31.2[2] | 1.9 | 34.3[3] |
| $C_{24}$ Acetal | 14.0 | 2.1 | 11.4 | 14.5 | 7.2 | 13.0 |
| Heavies | None Detected | Detected | None Detected | Heavies Present- Amt. Unknown | 0.9 | 11.8 |

● Product Selectivities and Yields:

|  | Run I | Run II[7] | Run III |
|---|---|---|---|
| + $C_{16}$ Selectivity[5] | 97 | 57 max | 51 |
| + ($C_8$ + $C_{16}$) Alcohol Yield[6] | 98+ | 67 max | 40 |

Notes:
[1]The product composition shown is on a heavies-free basis. Bottoms have been detected (by G.C.) in product produced by the conventional aldol reaction system; however, selectivity to heavies is not presently known.

[2]For Run II, ca. 30% of the components identified as $C_{16}$ Prod. do not correspond to components contained in the $C_{16}$ fraction obtained via the Aldox route to HDA or the new UFOA aldol process. These materials may not be alcohols or aldehydes.

[3]For Run III, ca. 25% of the components identified as $C_{16}$ Prod. do not correspond to components contained in the $C_{16}$ fraction obtained via the Aldox Route to HDA or the UFOA aldol process.

[4]Product reported on an IPA free basis.

[5]$C_{16}$ Selectivity $\equiv \dfrac{\text{Net } C_{16} \text{ Product Formed}}{(\text{Ald.} + \frac{1}{2} \text{Acetal}) \text{ decrease}} \times 100$:

[6]$(C_8 + C_{16})$ Alc. Yield $\equiv \dfrac{(C_{16}\text{OH Precursor} + C_8\text{HO} + \text{Net } C_8\text{OH}) \text{ Prod.}}{(C_{16}\text{OH Precursor} + C_8\text{HO} + \text{Acetal}) \text{ Feed}} \times 100$:

where: Net $C_8$OH = $C_8$OH in Prod. − $C_8$OH in Feed.

[7]Selectivity and Yield reported on heavies-free basis. Therefore, estimates represent maximum possible selectivity and yield for Run II.

TABLE III

| Feed | Run No. | Wt. %[2] Cat. | Prod. Distribution via. G.C. wt.% | | | | | Product[1] Selectivity (%) |
|------|---------|---------------|--------|--------|--------|--------|--------|--------|
| | | | Lights | $C_xHO$ | $C_zHO$ | $C_{2x}$ | Acetal | |
| $C_8HO$ | Feed[3] | — | 5.6 | 54.7 | 15.4 | 7.4 | 11.6 | — |
| $C_8HO$ | III-1 | 0.14 | 4.5 | 18.8 | 27.0 | 46.6 | 3.1 | 100. |
| $C_8HO$ | Feed | — | 10.5 | 49.0 | 24.0 | 2.6 | 14.0 | — |
| $C_8HO$ | III-2 | 0.04 | 11.0 | 25.1 | 29.6 | 32.5 | 1.8 | 100. |
| $C_8HO$ | Feed | — | 16.5 | 16.6 | 29.6 | 7.4 | 37.3 | — |
| $C_8HO$ | III-3 | 0.18 | 17.5 | 10.7 | 41.1 | 27.5 | 3.1 | 100. |

Notes:
[1]Prod. Selectivity = percentage of converted components to saleable product.

[2]Wt.% Cat. = Wt.% NaOH on feed.
[3]Trace heavy components detected in feeds and products.

Reaction Conditions:
* Reactor Type-Batch
* Type = 500° F
* Res. Time = 5 hrs.
* $H_2O$ = 5 vol.% on feed except = 3 vol.% (Run III-3)

EXAMPLE 4

In this Example carried out in the manner described for Example 3 above, the effect of catalyst source on selectivity was investigated.

The results found in Table IV show: (1) sodium hydroxide, acetate, or soaps (stearate, tallates, etc.) can be effectively employed as catalyst in UFOA reaction systems giving comparable integral reaction rates and product selectivities; (2) selectivity to dimer alcohol precursor much greater than 100% can be achieved (selectivity based on aldehyde content in feed, e.g., Run No. IV-1 with feed composition shown) with UFOA processing; (3) oxo feedstreams containing high acetal content can be efficiently utilized by UFOA processing; and (4) the precursor of octadecyl alcohol can be readily produced by employing the claimed invention using a crude oxo plant stream available during isononyl alcohol production.

EXAMPLE 5

In the manner described for Example 3 above, a series of experiments were carried out to determine the sensitivity of selectivity and integral product yield to reasonable variations in the ratio of aqueous base catalyst to oxo product feed. The results of these runs may be found in Table V and show that product selectivity is not measurably effected by varying aqueous catalyst to oxo product feed ratio ca. ±20% around a desired process operating point (e.g., conditions set forth in Run V-2 below).

TABLE V

CHANGES IN $H_2O$/CATALYST CONCENTRATION DO NOT MARKEDLY ALTER UFOA CONDENSATION SELECTIVITY, INTEGRAL REACTION RATE, OR PRODUCT YIELD

| Feed | Run No. | Vol. of 0.1N NaOH on Feed | Prod. Distribution via G.C. wt.% | | | | | Product[1] Select. (%) |
|------|---------|---------------------------|--------|---------|---------|----------|--------|--------|
| | | | Lights | $C_8HO$ | $C_8HO$ | $C_{16}$ | Acetal | |
| $C_8HO$ | Feed | — | 10.5 | 49.0 | 24.0 | 2.6 | 14.0 | — |
| $C_8HO$ | V-1 | 3.4 | 10.9 | 27.5 | 28.8 | 29.4 | 3.4 | 100. |
| $C_8HO$ | V-2 | 5.0 | 10.4 | 27.8 | 29.9 | 29.2 | 2.6 | 100. |
| $C_8HO$ | V-3 | 6.7 | 13.7 | 21.9 | 28.8 | 33.5 | 2.2 | 100. |

Notes:
[1]Product Selectivity = percentage of converted components to saleable product.
[2]Trace heavy components detected in feeds and products.

Reaction Conditions:
* Reactor Type-Batch
* T = 500° F
* Res. Time = 5 hours

EXAMPLE 6

In the manner described for Example 1 above, a series of runs were carried out to determine the effect of primary process variables on UFOA selectivity and reactivity. Data are presented in Table VI. Results indicate UFOA condensation of aldehydes can be carried over a broad range of temperature and catalyst levels without incurring measurable selectivity loss.

TABLE IV

CATALYSTS FOR UFOA CONDENSATION

| Feed | Run No. | Catalyst[2] | Prod. Distribution via G.C. wt. % | | | | | Product[1] Selectivity (%) |
|------|---------|-------------|--------|---------|---------|----------|--------|--------|
| | | | Lights | $C_8HO$ | $C_8OH$ | $C_{18}$ | Acetal | |
| $C_8HO$ | Feed | — | 16.5 | 16.6 | 29.6 | 7.4 | 37.3 | — |
| $C_8HO$ | IV-1 | Na Stearate | 17.4 | 9.7 | 40.9 | 27.2 | 4.7 | 100. |
| $C_8HO$ | IV-2 | Na Acetate | 17.5 | 10.6 | 41.6 | 26.8 | 3.5 | 100. |
| $C_8HO$ | IV-3 | NaOH | 17.3 | 10.4 | 41.1 | 26.9 | 4.2 | 100. |

Notes:
[1]Product Selectivity = percentage of converted components to saleable product.

[2]Cat. = 0.16 wt.% NaOH on feed or equivalent
[3]Trace heavy components detected in feed and products.

Reaction Conditions:
○ Reactor Type-Batch
○ T = 500° F
○ P = 550 psig
○ Res. Time = 5 hours
○ $H_2O$ = 3 vol.% on feed

TABLE VI

UFOA CONDENSATION GIVES HIGH SELECTIVITY WITH LOW RESIDENCE TIME

| Feed | Run No. | Wt. %[1] NaOH | Vol. %[1] $H_2O$ | Lights | $C_8HO$ | $C_8OH$ | $C_{16}$ | Acetal | Heavy | React. Temp. (°F) | Res. Time (hrs) | Prod. Select. (%) |
|---|---|---|---|---|---|---|---|---|---|---|---|---|
| $C_8HO$ | Feed | — | — | 15.7 | 41.7 | 21.2 | 4.4 | 17.1 | trace | — | — | — |
| $C_8HO$ | VI-1 | 0.45 | 2.0 | 13.0 | 15.8 | 35.3 | 32.7 | 3.3 | trace | 600. | 1.5 | 100. |
| $C_8HO$ | Feed | — | — | 10.5 | 49.0 | 24.0 | 2.6 | 14.0 | trace | — | — | — |
| $C_8HO$ | VI-2 | 0.2 | 4.0 | 6.0[2] | 30.5 | 29.6 | 31.3 | 2.6 | trace | 500. | 1.5 | 100. |
| $C_8HO$ | VI-3 | 0.1 | 2.0 | 7.5[2] | 36.6 | 26.1 | 26.5 | 3.3 | trace | 550. | 0.5 | 100. |

Notes:
[1]Catalyst and water levels based on $C_8HO$ Feed
[2]Lights lost during sampling

EXAMPLE 7

Example 7 illustrates a method of measuring the maximum level of water solubilizable in a crude oxo product, or an aldolization mixture, at a given temperature.

A 1,000 cc. static cell was charged with approximately 150 cc of water and 350 cc of an oxo product having a given conversion level, e.g., 25%, 50%, 75%, or 90%. The cell was rocked in a constant temperature bath to attain an equilibrium. After the equilibration, the agitation was stopped; and two phases, i.e. oil-rich and water-rich, were allowed to separate. Subsequently, a sample was withdrawn from the oil-rich phase for an analysis. The water content in this sample was then determined by a standard Karl Fischer titration method. Such measurements were conducted on a series of $C_9^=$ oxo products having the conversion rates of 25%, 50%, 75% and 90% at various temperature levels.

The data plotted on the accompanying Figure show that the water solubility in a $C_9^=$ oxo product rises rapidly with the increase in the temperature; and that the water solubilities in the $C_9^=$ oxo products of the four different conversion levels essentially converge to a maximal point at a temperature near 700° F.

What is claimed is:

1. An aldolization process which comprises contacting an aldehyde-containing feed with a catalyst, in an amount ranging from about 0.01 to about 3 weight percent based on the aldehyde-containing feed, selected from the group consisting of hydroxides, soaps, alkoxides and phenoxides of Groups I-A and II-A metals, quaternary ammonium hydroxides and choline in the presence of water in an amount substantially within the solubility limit of the aldehyde-containing feed at a temperature ranging from about 300° F. to about 1,000° F. to achieve a uniphase aldolization mixture.

2. The process of claim 1 wherein said basic catalyst is selected from the group consisting of sodium hydroxide, potassium hydroxide, sodium stearate, sodium acetate and benzyl trimethyl ammonium hydroxide.

3. The process of claim 2 wherein said basic catalyst is sodium hydroxide.

4. The process of claim 1 wherein said aldehyde-containing feed is a crude-demetalled oxo product.

5. The process of claim 4 wherein said oxo product comprises an acetal.

6. The process of claim 1 wherein said aldolization temperature ranges from about 500° F. to about 700° F.

7. A process for producing an aliphatic alcohol which comprises:

a. contacting an aldehyde-containing feed with a catalyst, in an amount ranging from about 0.01 to about 3 weight percent based on the aldehyde-containing feed, selected from the group consisting of hydroxides, soaps, alkoxides and phenoxides of Groups I-A and II-A metals, quaternary ammonium hydroxides and choline in the presence of water in an amount substantially within the solubility limit of the aldehyde-containing feed at a temperature ranging from about 300° F. to about 1000° F. to achieve a uniphase aldolization mixture; and, thereafter, b. hydrogenating the aldol product produced in (a) above under conventional conditions and using conventional catalysts to produce said aliphatic alcohol.

8. The process of claim 7 wherein said aliphatic alcohol product comprises hexadecyl alcohol.

* * * * *